United States Patent [19]

Mostofin et al.

[11] 4,012,278
[45] Mar. 15, 1977

[54] FEED WATER AND CONDENSATE SAMPLE ANALYZER FOR POWER PLANTS

[76] Inventors: Alexei Alexeevich Mostofin, ulitsa Karbysheva, 4, korpus 1, kv. 92; Nina Sergeevna Sorokina, ulitsa Dmitrievskaya, 10, kv. 1, both of Leningrad, U.S.S.R.

[22] Filed: Sept. 19, 1975

[21] Appl. No.: 615,075

[52] U.S. Cl. .................................. 159/30; 73/53; 159/43 R
[51] Int. Cl.² .................. G01N 27/42; B01D 1/02
[58] Field of Search ............. 73/61 R, 61.1 R, 53; 159/17 R, 17 P, 17 C, 30; 324/30 B

[56] References Cited
UNITED STATES PATENTS 3,542,113  11/1970  Mostofin et al. ............... 159/30

Primary Examiner—Richard C. Queisser
Assistant Examiner—Joseph W. Roskos

[57] ABSTRACT

A pressure column of the analyzer communicates with a concentrator made up of a plurality of series-connected evaporators. Arranged at the outlet of a first evaporator is an electroconductivity sensor whose output signal indicates ammonia concentration, and the first evaporator's throttle is provided with a passage aperture which is peferably 1.5 or 2 times less than the throttles of the other evaporators. Provided at the outlet of the last evaporator is another electroconductivity sensor whose output signal indicates the concentration of salts. Both sensors are optionally connected to a common recorder, thereby ensuring simultaneous recording of the concentration of both salts and ammonia.

3 Claims, 1 Drawing Figure

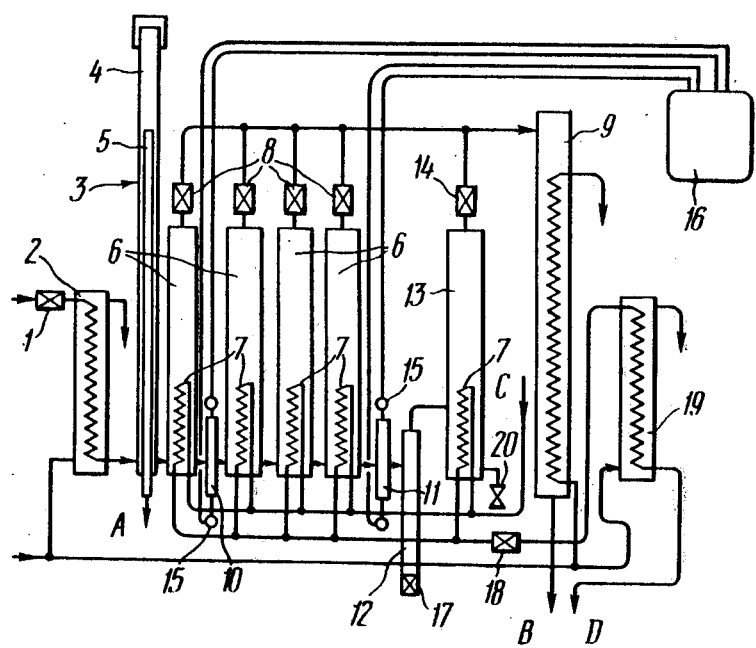

FEED WATER AND CONDENSATE SAMPLE ANALYZER FOR POWER PLANTS

The present invention relates to a feed water and condensate sample analyser for power plants and can be most effectively employed for determining the content of ammonia and salts in the working medium of thermal and atomic power stations.

Continuous and failure-proof operation of modern highcapacity power installations largely depends upon two main factors of the quality of the working medium, namely a minimum content of non-volatile ionic admixtures, "salts", and the maintenance of an optimum concentration of ammonia in water, the ammonia being a corrective agent.

An increase in the salt content leads to deterioration of the quality of the feed water and condensate streams thereby adversely affecting the reliability of operation. The increase may cause a premature shutdown of the equipment for chemical cleaning of both the steam generator and the turbine.

A deviation from the optimum content of ammonia in the feed water inevitably intensifies corrosion of the power plant components made from carbon steel or brass, which, in turn, causes formation and accumulation of deposits or corrosion products in the steam generating pipes of the boiler and the turbine.

Known in the art is a device for analysing condensate samples enriched with salts, e.g. one described in British Pat. No. 1,188,056. This device enables automatic determination of the content of salts in a degasified and concentrated sample. The device incorporates a pressure column ensuring pressure constancy in a concentrator and release of an excessive amount of the sample being taken. The pressure column communicates with the concentrator comprising four series-connected evaporators. Each evaporator is provided with a tubular heater and a throttle washer to limit the discharge of evaporated material. All the evaporators are linked with a common condenser wherein the steam which has been formed in the evaporators is condensed.

An electroconductivity sensor of the concentrated sample is provided with two stainless steel electrodes and arranged at the outlet of the fourth evaporator. Having passed through the sensor, the sample is fed via a hydraulic seal into one more evaporator having a throttle washer disposed at the steam outlet from this evaporator. This evaporator is intended for boiling down the concentrated sample which has left the sensor, and communicates with the condenser by the steam phase. Connected to the sensor with the aid of clamps is a salt-content recorder having a calibrated scale. The hydraulic seal ensures reliable operation of the sensor. A valve installed in the lower part of the hydraulic seal enables periodic selection of concentrated samples for chemical analysis.

A multi-stage washer throttle provided in front of the pressure column serves to limit the discharge of the sample being supplied to the analyser and to bring the sample pressure down to the atmospheric pressure level.

Another washer throttle is intended to let out the condensate of heating steam with an insignificant steam overshoot. Coolers serve to cool the sample being fed to the analyser and the heating steam being supplied from the heaters. The last evaporator is scavenged via the valve.

The principle of operation of such a device consists in that the concentration of salts is gradually increased in the sample passing through the concentrator, while the gas component is decreased. Thus, a concentrated sample which contains only salts is fed to the electroconductivity pickup, which makes it possible to effect automatic continuous control of the salt content in the power plants feed water and the condensate.

A disadvantage of the prior art device is that it does not permit to determine the concentration of feed water and the condensate of a corrective (compensating) agent, namely ammonia that is present in the samples. At the same time, as it has already been mentioned above, continuous and automatic measuring of ammonia concentration in feed water and condensate is of great practical importance for thermal and nuclear power engineering. The supply of ammonia into feed water should be thoroughly metered to maintain an optimum pH value at which the rate of corrosion of steel and copper-containing elements becomes minimum.

For thermal power stations operating on condensate, and atomic power stations with water-water reactors, the ratio of salts and ammonia in feed water and condensate is 0.5–1:10 on the average.

Therefore, it is possible to measure ammonia concentration with respect to the value of total electroconductivity of a sample of feed water or condensate.

To determine total electroconductivity there are known in the art special devices, conductometers, wherein a sample is fed after cooling to an electroconductivity sensor. A disadvantage of such devices is low reliability of obtaining comprehensive data on ammonia concentration due to the presence of carbonic acid in the samples being analysed, which also affects total conductivity. Another disadvantage of conductometers is the necessity of making a correction for the sample temperature for which there are employed special devices, thermal compensators.

It is an object of the present invention to provide a device for analysing samples of feed water and condensate of power plants, permitting, with the aid of a single sample, to simultaneously determine the concentration of both ammonia and salts.

Another object of the invention is to provide an analyser of samples of feed water and condensate of power plants, ensuring more reliable results of continuous determination of ammonia concentration.

Still another object of the invention is to provide a device for analysing samples of feed water and condensate of power plants, which enables the consumption of the samples being selected to be cut down.

With these and other objects in view, the inventive feed water and condensate sample analyser for power plants comprises a pressure column connunicating with a concentrator obtaining a concentrated sample at the outlet of the concentrator with a minimum content of gaseous components in the sample. The concentration is made up of a plurality of evaporators connected in series in the direction of flow of the liquid being analyzed. Each evaporator has throttle washers to remove a steam-gaseous mixture, and a concentrated sample electroconductivity sensor. It is important that the throttle of the first evaporator downstream of the sample flow has a smaller passage than in the other stages of evaporation so that in the first-stage evaporator there is maintained a lesser level of liquid and, consequently, a lesser amount of steam is generated, sufficient for heating the fluid up to the boiling point and for partial degassing thereof. Another electroconductivity sensor is provided between the first and the subsequent evaporators in the liquid phase flow with the result that the analyzer ensures simultaneous that the analyser ensures a possibility of simultaneously measurements of the salts and the ammonia content in the sample. The readings of both sensors are fed to a single secondary recorder.

Such a structural embodiment makes it possible to determine the concentration of both ammonia and salts in a single sample.

Other objects and advantages view of the present invention will be come more evident from the following detailed description of an exemplary embodiment thereof with reference to the appended drawing the sole FIGURE of which is a schematic of an analyser according to the invention.

A feed water or condensate sample taken by a sampling probe of a known design (not shown) passes through a multi-stage washer throttle 1 serving to limit the sample consumption and to decrease its pressure to the atmospheric level, and through a cooler 2, and is then taken to a pressure column 3 which ensures constant pressure in a concentrator and release of excessive amounts of the sample being selected. The pressure column is made in the form of a vertical tube 4 accommodating a second discharge tube 5 of a smaller diameter. The column outlet is connected to the concentrator including four series-connected evaporators 6 made in the form of vertical cylindrical tubes. Each evaporator has a tubular heater 7 with internal steam heating and a throttle washer 8 provided in the upper portion of the heater. The diameter of the passage aperture of the washer 8 in the first evaporator in the direction of the flow of the fluid being analyzed is somewhat smaller that that of the washers in the other evaporators, and the level of the fluid phase in that evaporator is so high as to ensure degassing of carbonic acid only. To ensure such degassing conditions, the diameter of the passage aperture of the washer 8 in the evaporator 6, the first one downstream of the fluid flow, is preferably 1.5 to 2 times less than in the passage washers of the other evaporators.

All the evaporators 6 are connected to a common condenser 9 wherein steam coming from the evaporators 6 of the concentrator is condensed.

An electroconductivity sensor 10 of the partially degassified sample need not be described in detail since such sensors are widely known and commercially available. Note should be made only of the fact that this sensor has two electrodes made of stainless steel, to be connected to an optional recorder to be described later. This sensor 10 is arranged at the outlet of the first evaporator 6 and communicates therewith and with the subsequent evaporator so that the sample leaving the first evaporator washes the sensor's electrodes and then goes to the second evaporator.

Another electroconductivity sensor 11 of the concentrated sample is also provided with two stainless steel electrodes and is arranged at the sample outlet from the fourth evaporator 6 of the concentrator. The outlet of the sensor 11 communicates via a hydraulic seal 12 with an evaporator 13 having a throttle limiting washer 14 provided at the steam outlet from an evaporator 13. The evaporator 13 is designed to boil down the concentrated sample which has left the sensor 11, and is connected to the condenser 9.

Connected to the sensors 10 and 11, via terminals 15, is a recorder 16 having two scales, namely, a scale showing the content of ammonia, and one showing the content of salts. The hydraulic seal 12 ensures reliable operation of the sensor 11. A valve 17 of the hydraulic seal makes it possible to periodically select the concentrated samples for chemical analysis.

A washer throttle 18 is intended to release the condensate of heating steam with an insignificant overshoot of the steam. A cooler 19 serves to cool the condensate of the heating steam coming out of the heaters 7. The evaporator 13 is periodically scavenged through a valve 20.

The inventive analyser operates as follows: The feed water or condensate sample passes through the multistage washer throttle 1, the cooler 2, and is fed into the pressure column 3, ensuring constant pressure in the evaporators 6 and 13 and release of excessive amounts of the selected sample into a return line (as is shown by arrow A).

After the pressure column 3, the sample passes at a definite pressure and blow rate through the evaporators 6 wherein it is successively boiled down. Secondary steam of each evaporator 6 and 13, after having passed through respective throttle washers 8 and 14, gets into the common condenser 9 operating at atmospheric pressure, wherein it is condensed and drained into the condensate return system (as is shown by arrow B).

The passage aperture of the throttle washer 8 of the first evaporator 6 has preferably a 1.5 to 2 times smaller diameter than in the other evaporation stages. Therefore, a lower level of fluid is maintained and a lesser amount of steam is generated in the first stage of evaporation than in the others. Steam yield of the first evaporator is made sufficient for heating the fluid up to a saturation point and for partial degassing thereof.

As experimental tests have shown, from the two gaseous components of ammonia and carbonic acid present in the sample, only carbonic acid, which dissolves much less than ammonia (approximately 1000 times in terms of volume), is removed essentially in the first evaporator, and a very insignificant part of the ammonia. Thus, the fluid sample at the output of the first evaporator contains only the salt component and the ammonia, while the ratio between the concentrations thereof actually corresponds to that in the initial sample where the ammonia concentration is more than 100 times greater than that of the salts. Therefore, a signal from the electroconductivity sensor 10 is indicative of the ammonia content in the sample with a high degree of accuracy.

A carbonic sample freed of acid at a stable temperature close to the saturation point is supplied after the first evaporator 6 into the electrical conductivity sensor 10 for the non-concentrated sample, and then into subsequent evaporators. Thus, a signal at the terminals 15 of the sensor 10 indicates the ammonia content in the sample. This signal is fed to the recorder 16.

A repeatedly boiled down and deeply degassified sample is supplied from the fourth evaporator into the electrical conductivity sensor 11 of the concentrated sample, then, via the hydraulic seal 12, into the final evaporator 13 to be finally boiled down.

The sample is boiled down with the aid of the heaters 7 having an internal steam heating. A Low-pressure saturated steam serves as a heating medium which is supplied to the evaporators 6 and 13 (along arrow C). The heating surfaces of the evaporators 6 and 13 have a reserve ensuring their operation under various pressures of the heating steam. The condensate of the latter, which has been developed inside the heaters 7, is removed via the washer throttle 18 into the cooler 19, then into the return system (along arrow D).

Multiple K of boiling down of the sample passing through the sensor 11 is equal to the relation of consumption G of the sample being supplied for the intensification to efficiency g of the evaporator 13, namely:

$$K = (G/g) = (F/f)$$

wherein
 $F$ is the total area of the apertures of all the washers 8 and 14; and
 $f$ is the area of the aperture of the washer 14 of the evaporator 13.

Such a simple relation stems from the fact that pressure drops and the condition of the heating steam for all the washers 8 and 14 is kept unchanged.

The pressure upstream of the throttle washers 8 and 14 is equal to that created by the pressure column 3, and downstream of the washers 8 and 14 it is equal to the atmospheric pressure.

In case pressure drops in any of the evaporators 6 and 13, the rate of delivery of the sample being boiled down will increase along with the growth of heat exchange intensity, while the efficiency and pressure at this stage will start growing and reach the rated values. The opposite will occur when the pressure increases above the rated value in any one of the evaporators 6 and 13.

Final boiling down of the selected sample takes place in the evaporator 13 where the concentration of the dissolved salts continuously grows and may attain such values when they begin precipitating. To preclude this, the evaporator 13 is provided with the valve 20 for periodic scavenging.

The recorder 16 serves to continuously measure the concentration of the ammonia and the salt content and has two scales calibrated, respectively, in units of ammonia concentration and units of salt (brine) content.

The scale of the brine gauge is calibrated from the estimated data, and the scale of the ammonia gauge is calibrated in keeping with the data of chemical analysis.

Incorporation of the proposed analysers in power units of the boiler-turbine type results in substantial annual savings of materials, including the cost of the sample saved and dispensing with two different chemical analysers, as were used earlier for the salt and the ammonia content.

What is claimed is:

1. A feed-water and liquid condensate sample analyzer for power plants, for a continuous analysis, comprising: a pressure column communicating with a concentrator for the sample, which produces at its outlet a sample with a minimum content of gaseous components of the sample being analyzed, and made up of a plurality of evaporators connected in series downstream of the phase flow of the sample; a throttle at the outlet of a steam-gaseous mixture of each of said evaporators; an electro-conductivity sensor at the outlet of said concentrator; said throttle of a first evaporator downstream of the sample flow having an aperture for the passage of the mixture, which aperture is smaller than apertures of said throttles of the other evaporators, and the size of said aperture is such that it ensures a level of a liquid phase so high as to ensure degassing of carbonic acid only; and a second electro-conductivity sensor between said first and said other evaporators, whose output is proportional to the content of ammonia in the liquid phase, with the result that the analyzer allows measurements of the content of both the salts and the ammonia in the process of the continuous analysis.

2. The analyzer as defined in claim 1, wherein said aperture of the throttle of the mixture of said first evaporator is 1.5 to 2 times smaller than said apertures of the throttles of said other evaporators.

3. The analyzer as defined in claim 1, further comprising a recorder to which both said electro-conductivity sensors are connected.

* * * * *